United States Patent [19]

Lafontaine

[11] 4,021,534
[45] May 3, 1977

[54] RADIOIMMUNOASSAY

[75] Inventor: George Stanford Lafontaine, Budd Lake, N.J.

[73] Assignee: Hoffmann-La Roche Inc., Nutley, N.J.

[22] Filed: Dec. 12, 1975

[21] Appl. No.: 640,114

[52] U.S. Cl. .................... 424/1; 23/230 B; 23/230.6; 424/12; 424/85; 424/88
[51] Int. Cl.² ................ G01N 33/00; A61K 39/00; G21H 5/02
[58] Field of Search ............ 424/1, 12, 1.5, 85, 424/88; 23/230 B, 230.6

[56] References Cited
UNITED STATES PATENTS

| | | | |
|---|---|---|---|
| 2,957,808 | 10/1960 | Campbell | 424/12 |
| 3,867,363 | 2/1975 | Hansen | 260/112 R |
| 3,867,518 | 2/1975 | Coffey et al. | 424/1 |

*Primary Examiner*—Benjamin R. Padgett
*Assistant Examiner*—Christine M. Nucker
*Attorney, Agent, or Firm*—Samuel L. Welt; Bernard S. Leon; Gerald S. Rosen

[57] ABSTRACT

Soluble antibody-antigen complexes with radiolabeled antigen are made insoluble and separated from soluble unreacted radiolabeled antigen by means of an insoluble complex of para-amino benzyl cellulose and an antibody to the antibody in the antibody-antigen complex.

8 Claims, 1 Drawing Figure

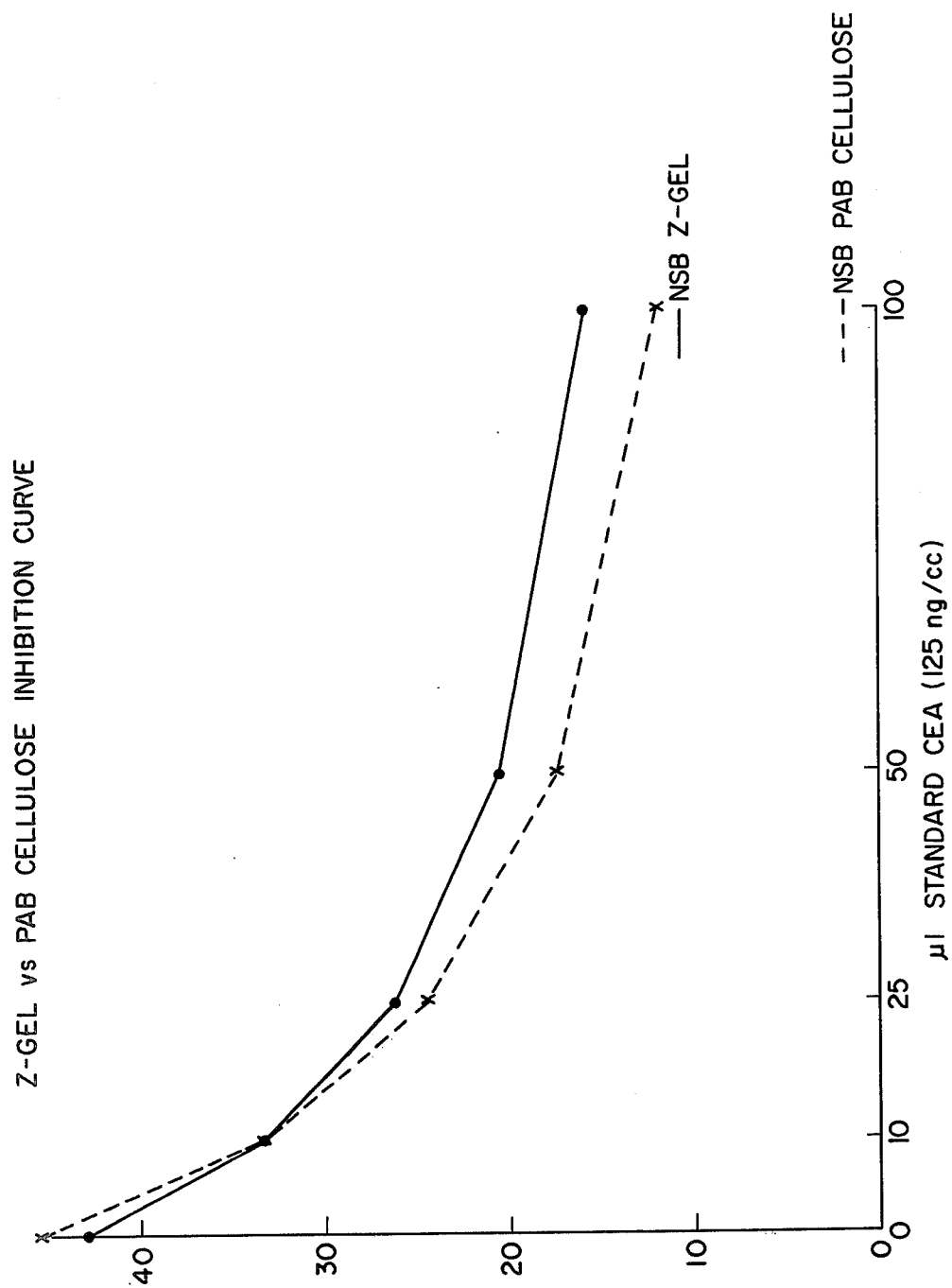

RADIOIMMUNOASSAY

BACKGROUND

In radioimmunoassay procedures one of the critical features in determining the results is the complete separation of the soluble radiolabeled antigen from soluble complexes of antibody bound to radiolabeled antigen. In effecting this separation it is known to utilize zirconyl phosphate gel (Z-gel). The Z-gel binds proteins when the pH of the Z-gel is equivalent to or below the isoelectric point of the proteins. Thus, the Z-gel depends upon the charge of the protein. This characteristic limits the applicability of Z-gel since all immunological systems do not have a charge at which Z-gel is effective for the desired separation.

Charcoal and other adsorbents are also deficient in separating the antibody-antigen complex from unreacted antigen since they are not sufficiently specific and have shortcomings of stripping. Precipitation methods, including double antibody methods are disadvantageous since their use results in a loss of material during aspiration and decantation, balancing the proportion of proteins to prevent non-specific binding and interference of sample constituents preventing precipitation by a second antibody.

There is thus a need for a system which provides complete separation of the antigen-antibody complex from the unreacted antigen without undesirable processing and specificity problems.

DESCRIPTION OF THE INVENTION

It has been discovered that by using a solid phase double antibody system, wherein the second antibody is bound to para-aminobenzyl cellulose, soluble antigen-antibody complexes can be insolubilized and separated completely from soluble antigens. Since the system used in this invention depends upon chemical reactions rather than electrical charges, its principle is applicable to a wide variety of immunological systems and is especially useful in the following radioimmunoassays, carcinoembryonic antigen (CEA), insulin, 1-thyroxine, 3-3'-5-triiodo-L-thryonine and the like.

Immunoglobulin G (IgG) is present in the gamma fraction of blood serum. It is composed of a group of proteins which act as antibodies. Each of the IgG proteins is specific to a particular antigen. IgG can also act as an antigen. For example, if injected into a goat, it causes the goat to form anti-IgG antibodies.

In the practice of this invention an IgG specific to the particular antigen of the immunological system which is subjected to radioimmunoassay procedures is used to form the antibody to that IgG. The antibody, i.e., the IgG, is considered the primary antibody whereas the antibody to IgG is considered the secondary antibody.

This invention, while widely applicable, will be exemplified in reference to the radioimmunoassay for carcinoembryonic antigen (CEA) wherein the primary antibody is IgG specific to CEA and the secondary antibody is specific to IgG.

The invention process involves the indirect radioimmunoassay procedure wherein the antigen or body fluid containing the antigen and a measured amount or radiolabeled antigen are incubated with the test solution containing the primary antibody. The reaction is stopped by reacting the resulting solution with a complex of para-aminobenzyl cellulose coupled to an antibody (secondary antibody) directed against the primary antibody. This causes immobilization of the antibody-antigen complex formed in the first incubation. The radioactivity of either the resulting solution or the resulting immobilized complex on cellulose is measured after the immobilized complex is removed from the solution by centrifugation or filtration and compared to a standard inhibition curve.

As used herein "soluble" means soluble in aqueous media and "insoluble" means insoluble in aqueous media.

In the radioimmunoassay for carcinoembryonis antigen, the primary antibody is formed by injecting an appropriate animal with CEA and subsequently obtaining the antiserum which is formed then fractionating it to isolate the IgG fraction. The secondary antibody is formed by injecting a second animal with the primary antibody subsequently obtaining the antiserum from the animal and fractionating it to isolate the IgG fraction which is then coupled to para-aminobenzyl cellulose.

The conventional indirect radioimmunoassay for CEA is then conducted and the incubation is stopped with the para-aminobenzyl cellulose coupled secondary antibody instead of the conventional Z-gel.

The coupling of the para-aminobenzyl cellulose to the secondary antibody is accomplished by a process which is a modification of that disclosed in U.S. Pat. No. 2,957,808. Thus, the secondary antibody is coupled to the para-aminobenzyl cellulose by diazotizing the cellulose then reacting the resulting product with the antibody in the cold at a basic pH. Usually, about 1 to 2% by weight antibody based on the weight of the product, is coupled to the para-aminobenzyl cellulose. Preferably about 1.5% is coupled. The resulting product is insoluble in water.

For use in the radioimmunoassay, the coupled antibody is suspended in a buffered solution at a pH of from about 7 to 8, preferably 7.4, in a predetermined excess to insure the completion of the reaction.

The resulting product is specific to the primary antibody, either when the primary antibody is complexed with the antigen, e.g., CEA, or when it is unreacted.

BRIEF DESCRIPTION OF THE DRAWING

FIG. 1 is an inhibition curve of radioimmunoassays employing Z-gel and para-amino benzyl cellulose.

The following Examples illustrate the invention.

EXAMPLE 1

Preparation of anti-goat IgG

One donkey and 10 New Zealand white rabbits were immunized with DEAE purified goat IgG. Animals received goat IgG injections every 2 weeks for a total of 10 injections. The goat IgG in physiological phosphate buffer was emulsified with an equal volume of Freund's complete adjuvant for single site injections. Following the 5th injection, sample bleedings were taken prior to each subsequent injection for monitoring antibody titer by primary antibody neutralization. The anti-goat IgG sera were ammonium sulfate fractionated six times with 1/3 saturation and exhaustively dialyzed against deionized water during a 72 hour period. The fractionated sera were then dialyzed against 0.15 M borate-buffered saline, pH 8.9, for 4 hours and centrifuged at 1500 × G at 4° C. for 30 minutes to remove aggregated globulin. Anti-IgG reacts immunologically with the antibody portion of the CEA antibody-CEA complex.

EXAMPLE 2

Preparation of para-aminobenzyl cellulose bound anti-IgG

Para-aminobenzyl cellulose was diazotized and coupled to anti-IgG according to the process of U.S. Pat. No. 2,957,808. The diazotization was accomplished by reacting para-aminobenzyl cellulose with sodium nitrite in aqueous acid medium and recovering the resulting precipitate. The coupling of the diazotized para-aminobenzyl cellulose to anti-IgG was accomplished as follows: The precipitate is washed with distilled water and graded into two fractions, one a relatively coarse material normally used in column chromatography which was separated from the finer fractions by sedimentation. The other fraction which remained suspended for at least 15 minutes was used for antibody coupling. The remaining material was discarded.

The suspended para-aminobenzyl cellulose fraction was reacted with an ice-cooled solution of anti-IgG in borate buffer of pH 8.75. The amount of anti-IgG used was, on a dry weight basis, about one-tenth the weight of para-aminobenzyl cellulose. The reaction was allowed to proceed in an ice bath for two hours, then the pH was adjusted to 7.3 and the mixture was stored in the cold (about 4° C.) for about 36 hours. The resulting product which was recovered contained about 0.5% by weight antibody. Any remaining unreacted diazonium groups were protected by reaction with beta-naphthol. Sufficient amount of the antibody bound para-aminobenzyl cellulose was suspended in phosphate buffered saline at pH 7.4 to provide, in 2.0 ml., a predetermined excess.

EXAMPLE 3

CEA Radioimmunoassay a. Z-Gel—All tubes were run in sextuplicate and randomly divided into 2 groups of 3 each after the final incubation step. 0.5 Ml. of human plasma taken in liquid EDTA containing sorbate was diluted with 2.0 ml. of saline. The solution was extracted with a 2.5 ml. aliquot of cold 1.2 M perchloric acid and centrifuged for 20 minutes at 1000 × G. The supernatant containing the extracted CEA was dialyzed 4 times against 50 volumes of deionized water and finally dialyzed against 0.01 M ammonium acetate buffer, pH 6.5. The dialyzed plasma sample was incubated with 25 microliters of the appropriate goat anti-CEA serum dilution for 30 minutes at 45° C. followed by addition of $^{125}$I-labeled CEA and incubated again as just described. The reaction was stopped with a 2.5 ml. aliquot of Z-gel, quickly centrifuged for 5 minutes at 1000 × G, washed once in 5 ml. of 0.1 M ammonium acetate, pH 6.25, centrifuged, decanted, and counted in a gamma scintillation counter. Results were compared to a standard curve prepared in a synthetic medium matching the properties of extracted and dialyzed human plasma.

b. Double Antibody—All tubes were run in sextuplicate and randomly divided into 2 groups of 3 each after the final incubation step. 0.5 Ml. of human plasma taken in liquid EDTA containing sorbate was diluted with 2.0 ml. of saline. The solution was extracted with a 2.5 ml. aliquot of cold 1.2 M perchloric acid centrifuged for 20 minutes at 1000 × G. The supernatant containing the extracted CEA was dialyzed 4 times against 50 volumes of deionized water and finally dialyzed against 0.01 M ammonium acetate buffer, pH 6.5. The dialyzed plasma sample was incubated with 25 microliters of the appropriate goat anti-CEA serum dilution for 30 minutes at 45° C. followed by addition of $^{125}$I-labeled CEA and incubated again as just described. 0.5 Ml. of 10x phosphate buffered saline (PBS) was added to each tube to stop the primary antigen-antibody reaction to CEA; 2.0 ml. of cellulose-bound anti-goat IgG in 0.15 M phosphate buffered saline, pH 7.4, was added to each tube, stoppered and allowed to rotate 60 minutes at room temperature on a multi-purpose rotator. Five ml. of PBS was added to each tube followed by centrifugation at 1500 × G for 10 minutes. The supernatant fluid was gently decanted and the pellets washed in 10 ml. of PBS, centrifuged and decanted as before, taking care not to disturb the final pellet. Tubes were immersed in a water bath to rinse off any contaminating radioactivity, wiped clean, counted on a gamma counter along with the tube set containing the zirconyl phosphate gel pellets. Results are compared to a standard curve prepared in a synthetic medium matching the properties of extracted and dialyzed human plasma.

The CEA radioimmunoassay is an ion-sensitive, and to a lesser degree pH independent reaction. Z-gel of pH 6.25 essentially stops the reaction when added after 30 minutes incubation at 45° C.

When adding para-aminobenzyl cellulose anti-IgG instead of Z-gel, the reaction stops upon the addition of either 0.15 PBS pH 7.4 or 0.15 M ammonium acetate, pH 6.25. With 60 minutes additional incubation the primary antibody to CEA complexed with the immobilized second antibody. This, however, did not result in any detectable increase of complexing anti-CEA with the labeled antigen.

The results of the two radioimmunoassays are shown in the inhibition curve of FIG. 1.

Table 1 shows the raw CPM (counts per minute) of the 2 inhibitions curves with the CPM of the corresponding NSB substracted from each reference count. The data and FIG. 1 show that the method of this invention results in higher CPM than those resulting from the Z-gel process.

TABLE 1

| Reference point of inhibition curve: microliters of CEA standard* | CPM:*** Z-gel Method | CPM: PAB Cellulose Method | CPM: Z-gel-CPM NSB(Z-gel) | CPM: PAB Cellulose-CPM NSB(PAB Cellulose) | CPM: Difference in CPM between Z-gel-NSB vs. PAB Cellulose-NSB | CPM: Captured from Z-Gel Supernatant by PAB Cellulose |
|---|---|---|---|---|---|---|
| 0 | 43000 | 44500 | 32500 | 42750 | 10250 | 8000 |
| 10 | 33500 | 33500 | 23000 | 31750 | 8750 | 7500 |
| 25 | 26250 | 24500 | 15750 | 22750 | 7000 | 6750 |
| 50 | 20500 | 17500 | 10000 | 15750 | 5750 | 5500 |
| 100 | 16000 | 12000 | 5500 | 10250 | 4750 | 4500 |

TABLE 1-continued

RAW CPM DATA Z-GEL VS. PAB CELLULOSE

| Reference point of inhibition curve: microliters of CEA standard* | CPM:*** Z-gel Method | CPM: PAB Cellulose Method | CPM: Z-gel-CPM NSB(Z-gel) | CPM: PAB Cellulose-CPM NSB(PAB Cellulose) | CPM: Difference in CPM between Z-gel-NSB vs. PAB Cellulose-NSB | CPM: Captured from Z-Gel Supernatant by PAB Cellulose |
|---|---|---|---|---|---|---|
| NSB* | 10500 | 1750 | 0 | 0 | 0 | — |

*CEA standard concn. 125 mg/ml.
**NSB - nonspecific binding of $^{125}$I-CEA onto Z-gel or PAB cellulose
***CPM rounded off to nearest 250

I claim:

1. A method of insolubilizing soluble antigen-antibody complexes which comprises reacting said antigen-antibody complex in solution with a second antibody directed against the antibody in the soluble antigen-antibody complex said second antibody being bound to para-aminobenzyl cellulose.

2. A method of separating soluble antigen-antibody complexes from soluble antigen contained in said complex which comprises insolubilizing said antigen-antibody complex by reacting said antigen-antibody complex in solution with a second antibody directed against the antibody in the soluble antigen-antibody complex, said second antibody being bound to para-aminobenzyl cellulose, and separating the insolubilized complex.

3. In an indirect radioimmunoassay procedure, wherein a radiolabeled antigen complexed with its antibody is separated from unreacted radiolabeled antigen, the improvement which comprises insolubilizing the antigen-antibody complex by reacting it with a second antibody directed against the antibody in the antigen-antibody complex, said second antibody being bound to para-aminobenzyl cellulose.

4. The method of claim 1 wherein the antigen is carcinoembryonic antigen.

5. The method of claim 3 wherein the radiolabeled antigen is carcinoembryonic antigen labeled with iodine-125.

6. The method of claim 3 wherein the second antibody is anti-IgG.

7. Anti-IgG bound to para-aminobenzyl cellulose.

8. An antigen-antibody complex consisting essentially of as the antibody anti-IgG bound to para-aminobenzyl cellulose and as the antigen the complex of carcinoembryonic antigen and its antibody.

* * * * *